(12) United States Patent
Tsuyuki

(10) Patent No.: US 6,876,720 B2
(45) Date of Patent: Apr. 5, 2005

(54) X-RAY COMPUTED TOMOGRAPHY APPARATUS

(75) Inventor: Masaharu Tsuyuki, Nasu-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/281,988

(22) Filed: Oct. 29, 2002

(65) Prior Publication Data

US 2003/0108149 A1 Jun. 12, 2003

(30) Foreign Application Priority Data

Dec. 20, 2001 (JP) ........................................ 2001-388278
Jul. 2, 2002 (JP) ........................................ 2002-193939

(51) Int. Cl.⁷ .............................................. A61B 6/00
(52) U.S. Cl. .............................................. 378/8; 378/4
(58) Field of Search ...................................... 378/4–20

(56) References Cited

U.S. PATENT DOCUMENTS

| 5,459,769 | A |   | 10/1995 | Brown ........................... 378/4 |
| 5,594,772 | A |   | 1/1997 | Toki et al. .................... 378/114 |
| 5,612,985 | A |   | 3/1997 | Toki et al. ..................... 378/4 |
| 6,068,595 | A |   | 5/2000 | Miyazaki et al. ........... 600/410 |
| 6,188,744 | B1 | * | 2/2001 | Shinohara et al. ............. 378/8 |
| 6,236,706 | B1 |   | 5/2001 | Hsieh ............................ 378/8 |
| 6,289,075 | B1 |   | 9/2001 | Marume ........................ 378/8 |
| 6,337,992 | B1 | * | 1/2002 | Gelman ...................... 600/425 |

FOREIGN PATENT DOCUMENTS

| JP | 2624927 | 4/1997 |
| JP | 10-211198 | 8/1998 |
| WO | WO 98/32376 | 7/1998 |

* cited by examiner

*Primary Examiner*—Craig E. Church
*Assistant Examiner*—Jurie Yun
(74) *Attorney, Agent, or Firm*—Oblon, Spivak, McClelland, Maier & Neustadt, P.C.

(57) ABSTRACT

An X-ray computed tomography apparatus monitors the density of a contrast medium injected into a subject with a CT value by a preparation scan so as to adjust the main scan start timing. A guidance output unit outputs guidance to the subject. A control unit compares the CT value of tomographic image data obtained by the preparation scan with the first threshold, supplies guidance data to the guidance output unit to output the guidance to the subject when the CT value has reached the first threshold. The control unit compares the CT value of the tomographic image obtained by the preparation scan with the second threshold different from the first threshold, and starts executing the main scan or preparing the execution of the main scan when the CT value has reached the second threshold.

17 Claims, 11 Drawing Sheets

Extracting X% of pixels whose CT values are high from pixels within ROI

X-RAY COMPUTED TOMOGRAPHY APPARATUS

CROSS-REFERENCE TO RELATED APPLICATIONS

This application is based upon and claims the benefit of priority from the prior Japanese Patent Application No. 2001-388278, filed Dec. 20, 2001; and No. 2002-193939, filed Jul. 2, 2002, the entire contents of both of which are incorporated herein by reference.

BACKGROUND OF THE INVENTION

1. Field of the Invention

The present invention relates to an X-ray computed tomography apparatus having the function of monitoring the flow of a contrast medium into a region of interest by a preparation scan.

2. Description of the Related Art

In contrast medium imaging, it is important to perform a scan (main scan) at a proper timing when the contrast medium injected into a subject to be examined flows into a target slice. For this reason, a scan (preparation scan) at a dose lower than that for the main scan and image reconstruction with a low resolution are repeated before the main scan. When an imaging operator visually checks the density of contrast medium at the region of interest of a tomographic image and recognizes that the density has reached a certain level, the operator inputs a trigger for the main scan. Upon reception of the trigger, the apparatus stops the preparation scan and starts the main scan.

Figure 1A:
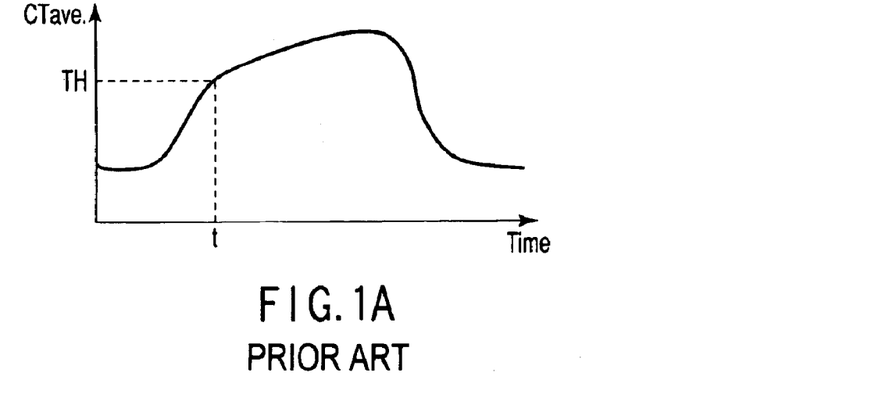
FIG. 1A is a graph showing a time density curve in the prior art.

Recently, a technique called a real preparation scan, which automatically sets a main scan start timing, has been widely used. According to this technique, as shown in FIG. 1A, the CT value of a region of interest is extracted from the tomographic image data obtained by a preparation scan, and the extracted value or an average CTave. is compared with a threshold TH. At time $t$ when the CT value or average CTave. has reached the threshold TH, a shift from the preparation scan to the main scan is started.

In a diagnosis, a doctor sees the consecutive tomographic images acquired by the main scan as a moving image, and in many cases, objectively checks variations in the contrast medium density of the region of interest over time with a time density curve. This operation is a so-called dynamic study.

The precision of this dynamic study is susceptible to the movement of the tissue due to breathing and pulsation as well as the body movement of a subject to be examined. The precision is affected more as the size of the region of interest decreases.

Figure 1B:
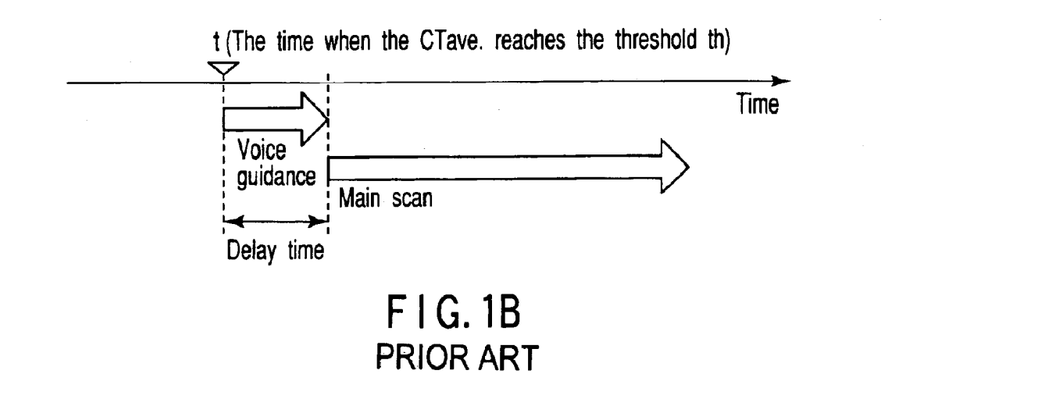
FIG. 1B is a view showing a delay time in a main scan in the prior art.

For this reason, before the main scan, the examiner instructs the subject to hold his/her breath and suppress body movement by using a loudspeaker or the like. An apparatus for automatically outputting such instructions has also been developed. In this apparatus, voice data about breath holding, suppression of body movement, and the like are held. As shown in FIG. 1B, at time $t$ when the CT value or average CTave. has reached the threshold TH, the voice data is played back (voice guidance).

In this case, however, the main scan starts with a delay corresponding to the time required to play back the voice data from time $t$ when the CT value or average CTave. has reached the threshold TH.

BRIEF SUMMARY OF THE INVENTION

It is an object of the present invention to reduce a delay of the main scan start timing in an X-ray computed tomography apparatus.

According to the first aspect of the present invention, there is provided an X-ray computed tomography apparatus which monitors a density of a contrast medium injected into a subject to be examined with a CT value or a value derived therefrom by a preparation scan so as to adjust a main scan start timing that differs in scan condition from the preparation scan, comprising a guidance output unit configured to output guidance to the subject, and a control unit configured to compare a CT value of tomographic image data obtained by the preparation scan or a value derived therefrom with a first threshold, supply guidance data to the guidance output unit or control the guidance output unit to output the guidance to the subject when the CT value or the value derived therefrom has reached the first threshold, compare the CT value of the tomographic image obtained by the preparation scan or the value derived therefrom with a second threshold different from the first threshold, and start executing the main scan or preparing the execution of the main scan when the CT value or the value derived therefrom has reached the second threshold.

According to the second aspect of the present invention, there is provided an X-ray computed tomography apparatus which monitors a density of a contrast medium injected into a subject to be examined with a CT value or a value derived therefrom by a preparation scan so as to adjust a main scan start timing that differs in scan condition from the preparation scan, comprising a control unit configured to compare a CT value of tomographic image obtained by a preparation scan or a value derived therefrom with a plurality of thresholds including a threshold for adjusting a main scan start timing.

According to the third aspect of the present invention, there is provided an X-ray computed tomography apparatus which monitors a density of a contrast medium injected into a subject to be examined with a CT value or a value derived therefrom by a preparation scan so as to adjust a main scan start timing that differs in scan condition from the preparation scan, comprising an X-ray tube, an X-ray detector, a high voltage generating unit configured to apply a high voltage to the X-ray tube, a reconstructing unit configured to reconstruct tomographic image data on the basis of an output from the X-ray detector, an operation unit configured to set a region of interest with respect to the tomographic image data, and a control unit configured to compare a CT value of some pixels in the region of interest or a value derived therefrom with a threshold, and stop the preparation scan and starts executing the main scan or preparing for the execution when the CT value or a value derived therefrom reaches the threshold.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An X-ray computed tomography apparatus (X-ray CT apparatus) according to an embodiment of the present invention will be described below with reference to the views of the accompanying drawing. Note that X-ray CT apparatuses include various types of apparatuses, e.g., a rotate/rotate-type apparatus in which an X-ray tube and X-ray detector rotate together around a subject to be examined, and a stationary/rotate-type apparatus in which many detection elements arrayed in the form of a ring are fixed, and only an X-ray tube rotates around a subject to be examined. The present invention can be applied to either type. In this case, the rotate/rotate type, which is currently the mainstream, will be exemplified.

In order to reconstruct one-slice tomographic image data, 360° projection data corresponding to one rotation around a subject to be examined is required, or (180°+view angle) projection data is required in the half scan method. In order to increase the reconstruction rate, this apparatus may use the technique disclosed in Jpn. Pat. Appln. KOKOKU Publication No. 1-23136, Jpn. Pat. Appln. KOKAI Publication Nos. 4-266744 and 12-70257, and the like. The present invention can be applied to either of these reconstruction schemes. In this case, the half scan method will be exemplified.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and movement of the electron-hole pairs to an electrode, i.e., a photoconductive phenomenon. As an X-ray detection element, either of these schemes can be used. In this case, the former type, i.e., the indirect conversion type, will be exemplified.

Recently, with advances toward the commercialization of a so-called multi-tube type X-ray CT apparatus having a plurality of pairs of X-ray tubes and X-ray detectors mounted on a rotating ring, related techniques have been developed. The present invention can be applied to both a conventional single-tube type X-ray CT apparatus and a multi-tube type X-ray CT apparatus. The single-tube type X-ray CT apparatus will be exemplified here.

Figure 2:
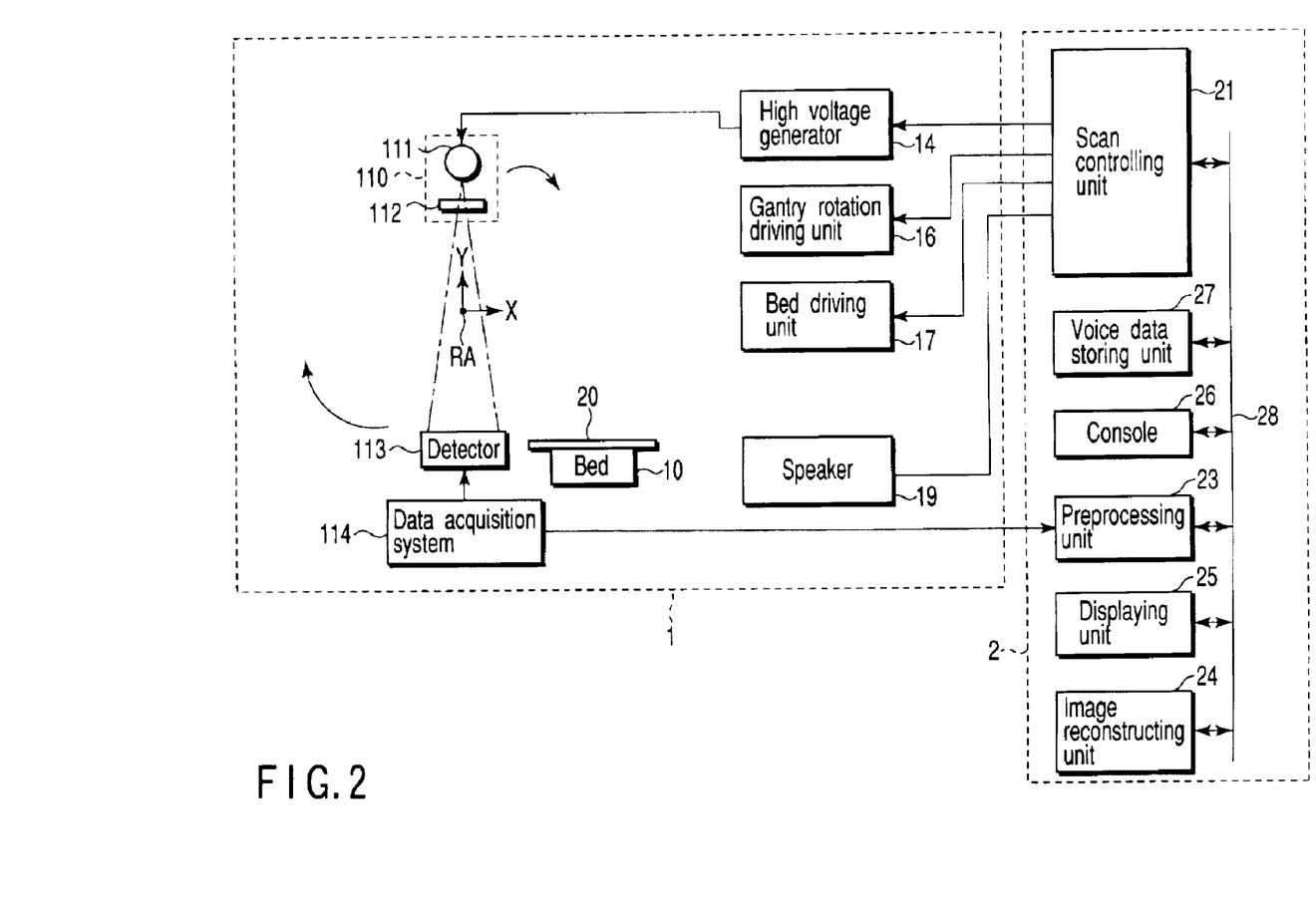
FIG. 2 is a block diagram showing the arrangement of the main part of an X-ray computed tomography apparatus according to an embodiment of the present invention.

FIG. 2 shows the arrangement of the main part of an X-ray computed tomography apparatus according to this embodiment. The X-ray computed tomography apparatus according to this embodiment is comprised of a scan gantry 1 and computer device 2. The scan gantry 1 is a constituent element for acquiring projection data about a subject to be examined. This projection data is loaded into the computer device 2 and subjected to processing such as image reconstruction real preparation. The computer device 2 is comprised of a scan controlling unit 21 and the following units connected to it via a clamping bolt 28: a preprocessing unit 23, image reconstructing unit 24, displaying unit 25, console 26, and voice data storing unit 27.

The subject is inserted into the cavity (imaging port) of the scan gantry 1 while lying on a table-top 20 of a bed 10. The table-top 20 of the bed 10 is driven by a bed driving unit 17 to move along the longitudinal direction. In general, the bed 10 is installed such that this longitudinal direction becomes parallel to a rotation axis RA (coinciding with the body axis and Z-axis) (to be described later). An annular rotating gantry (not shown) is mounted on the scan gantry 1 so as to be driven by a gantry rotation driving unit 16 to rotate about the rotation axis RA. An X-ray tube assembly 110 and X-ray detector 113 are so mounted on this rotating gantry as to face each other.

The X-ray tube assembly 110 is comprised of an X-ray tube 111 and an X-ray filter 112 for removing low-energy components to reduce the exposure dose. An inverter type high voltage generating units 14 is provided to supply power to the X-ray tube 111. The high voltage generating unit 14 includes a tube voltage switch, filament current switch, and the like to adjust a tube voltage and filament current arbitrarily or stepwise, in addition to a high voltage transformer, filament current generator, rectifier, and the like.

An output from the X-ray detector 113 is supplied as projection data to the image reconstructing unit 24 via a data acquisition system 114, a slip ring (not shown) which allows continuous rotation, and the preprocessing unit 23. This data is used for the reconstruction processing of tomographic image data. This tomographic image data is displayed on the displaying unit 25 and supplied to the scan controlling unit 21 to be used for the processing of determining the voice guidance generation timing and main scan operation start timing as will be described later.

The console 26 is provided to allow the operator to input various information such as scan conditions and real preparation conditions (two types of thresholds THguide and THmain and waiting time WT) and various instructions. The console 26 has an operation screen. On this operation screen or displaying unit 25, a setting window optimally designed to support the operator to set the above read preparation conditions is displayed by the scan controlling unit 21.

Real preparation imaging operation by the scan controlling unit 21 will be described below. In practice, before real preparation imaging operation, imaging slice positioning is done and the following are set: preparation scan conditions (tube voltage, tube current, scan time, and the number of channels bundled), main scan conditions (tube voltage, tube current, scan time, and the number of channels bundled), real preparation conditions (the size and position of a region of interest ROI, two types of thresholds THguide and THmain, and waiting time WT). Typically, in order to make the radiation quality uniform, a preparation scan tube voltage is set to be equal to a main scan tube voltage, whereas in order to suppress the exposure dose, a preparation scan tube current is set to be smaller than a main scan tube current. Setting of real preparation conditions will be described later. Real preparation imaging operation will be described first.

Figure 3:
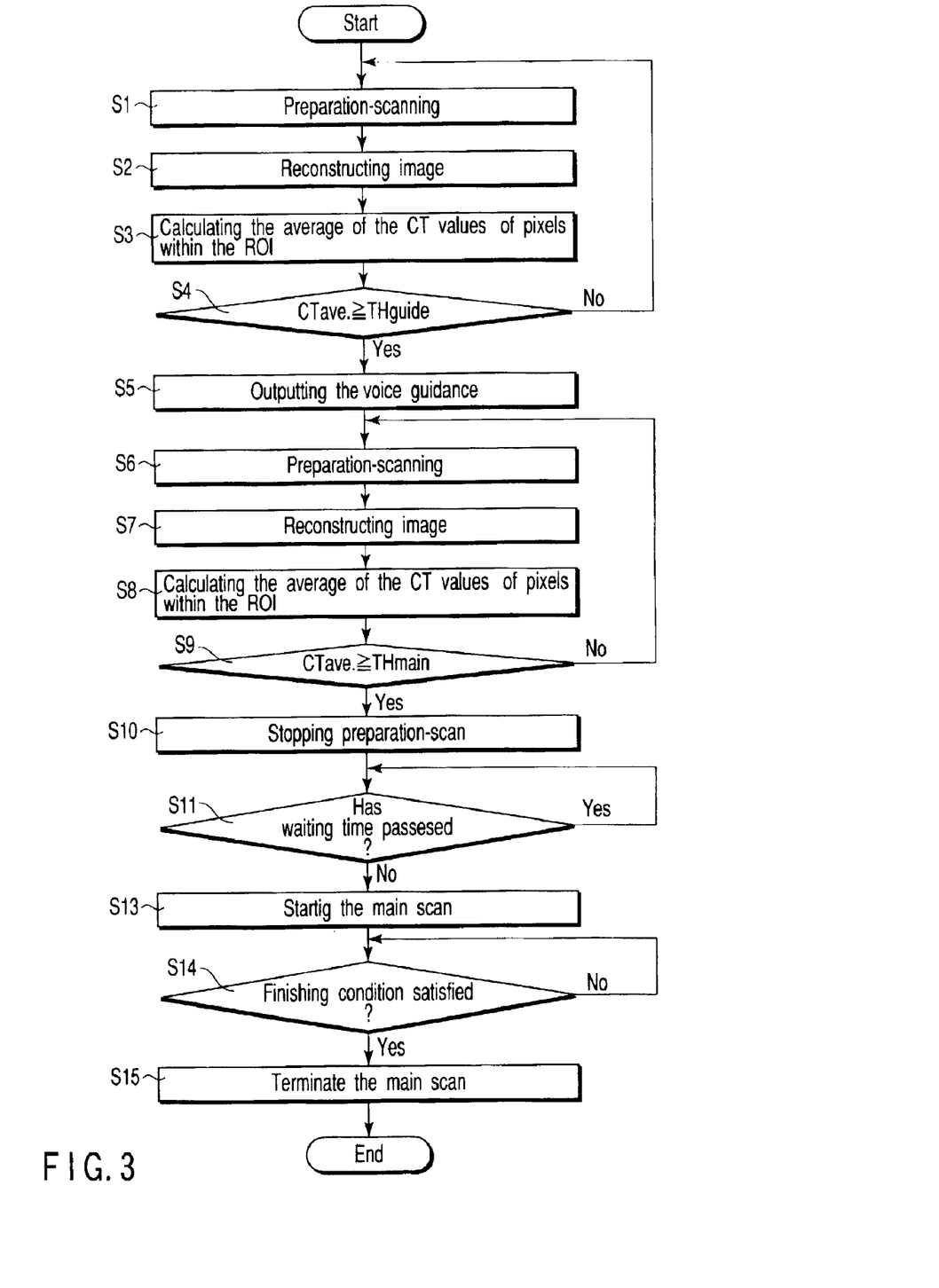
FIG. 3 is a flow chart showing operation from a preparation scan start to a main scan end according to this embodiment.
Figure 4:
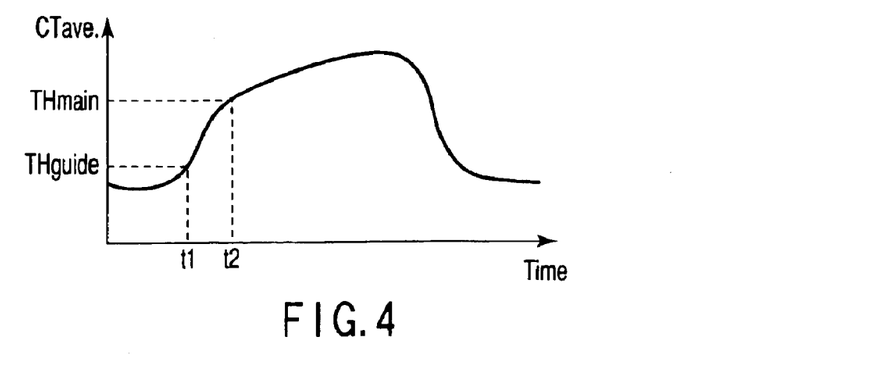
FIG. 4 is a graph showing a time density curve and two types of thresholds set therefor according to this embodiment.
Figure 5A:
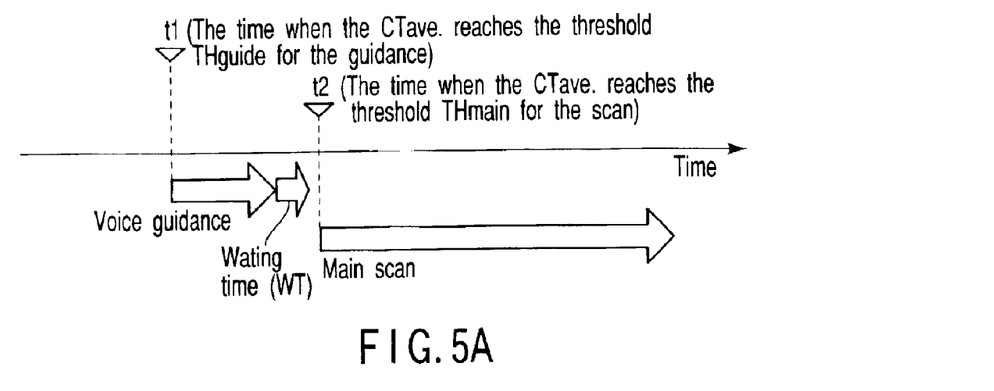
FIG. 5A is a timing chart showing operation from a preparation scan start to a main scan end according to this embodiment.
Figure 5B:
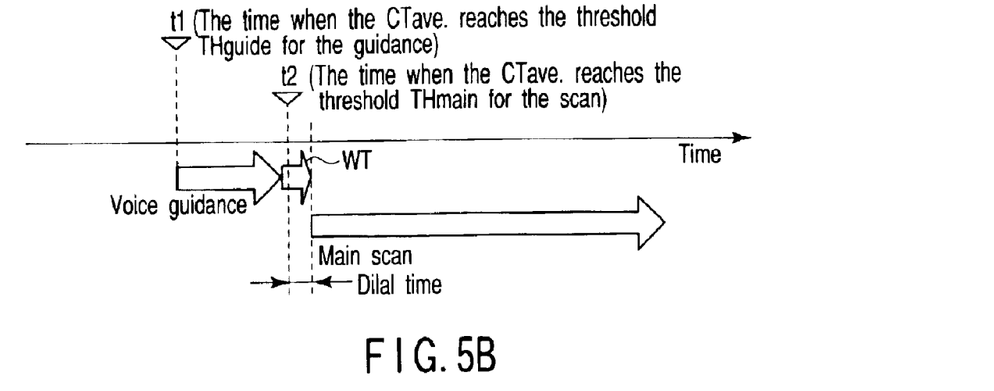
FIG. 5B is a timing chart showing a delay time of a main scan start according to this embodiment.

FIG. 3 shows a procedure for this operation. Refer to FIGS. 4 and 5A as well as FIG. 3. A real preparation scan is performed under the control of the scan controlling unit 21 under typical scan conditions, i.e., at a low dose and low resolution (adjacent channel bundling may be done) as compared with a main scan (S1). That is, with respect to a positioned slice, while the X-ray tube assembly 110 and X-ray detector 113 continuously rotate around a subject to be examined, X-rays are generated continuously or in a pulse-like manner, thereby cyclically repeating data acquisition.

Along with the preparation scan, the scan controlling unit 21 controls the image reconstructing unit 24 to reconstruct a CT value distribution as tomographic image data in real time from the projection data obtained by the preparation scan (this operation is called real-time CT) (S2). The scan controlling unit 21 extracts a plurality of pixels in a preset region of interest ROI from the tomographic image data obtained in step S2, and calculates an average CTave of the CT values of the extracted pixels (S3). The scan controlling unit 21 then compares the calculated CT average CTave with a preset threshold THguide for guidance which is lower than a threshold THmain for a shift to a main scan (S4).

Note that this CT average CTave reflects a contrast medium density, but a contrast medium density itself may be calculated by calculating the difference between a mask image acquired before the injection of the contrast medium and the real or live image data obtained by the preparation scan, extracting a plurality of pixels in the region of interest ROI from the differential image, and calculating the average of the pixels values.

In addition, a value other than the average CTave may be used as long as it is a characteristic value derived from the CT values of pixels in the region of interest ROI. For example, the median or maximum value of the CT values of pixels in the region of interest ROI or the half-width of a CT value—pixel count distribution may be used.

If the comparison reveals that the CT average CTave has not reached the threshold THguide for guidance, it is determined that the degree of staining of the region of interest attained by the contrast medium is too low, and the processing in steps S1 to S4 is repeated. At time t1 when the CT average CTave has reached the threshold THguide for guidance, the scan controlling unit 21 determines that the degree of staining of the region of interest attained by the contrast medium is in a state immediately before a main scan, and reads out voice data about breath holding and body movement suppression from the voice data storing unit 27. The scan controlling unit 21 then converts the data into a voice signal and supplies it to a speaker 19. As a consequence, guidance concerning breath holding and body movement suppression is output by voice to the subject (S5).

According to the above description, the guidance concerning breath holding and body movement suppression is done by voice. In place of this operation or in combination with it, however, guidance concerning breath holding and body movement suppression may be output as a character message or design on a display installed at a position where the subject can visually recognize the guidance and which is located outside an X-ray emission range.

Subsequently, the scan controlling unit 21 continues the preparation scan (S6), real-time image reconstruction (S7), and calculation of the CT average CTave of pixels in the region of interest ROI (S8), and compares the CT average CTave with the present threshold THmain for a shift to a main scan, which is higher than the threshold THguide for guidance (S9). If the comparison reveals that the CT average CTave has not reached the threshold THmain for a shift to a main scan, the scan controlling unit 21 determines that the degree of staining of the region of interest attained by the contrast medium is too low for a shift to a main scan, and repeats the processing in steps S6 to S9. At time t2 when the CT average CTave has reached the threshold THmain for a shift to a main scan, the scan controlling unit 21 determines that the degree of staining of the region of interest attained by the contrast medium has satisfied the condition for the shift to the main scan, and stops the preparation scan (S10).

At time t2 when the CT average CTave has reached the threshold THmain for a shift to a main scan, the scan controlling unit 21 finishes the voice guidance, and checks whether the waiting time WT prepared as a preparation period for the subject to hold breach and suppress body movement has elapsed since the end of voice guidance (S11). If the voice guidance has finished and the waiting time WT has elapsed, the scan controlling unit 21 starts a main scan (S13).

At time t2 when the CT average CTave has reached the threshold THmain for a shift to a main scan, if the voice guidance has not finished or the waiting time WT has not elapsed since the end of the voice guidance, the scan controlling unit 21 postpones a main scan until the voice guidance finishes and the waiting time WT elapses since the end of the voice guidance, instead of immediately starting the main scan at time t2 (S12). Such a situation occurs when the threshold THmain for a shift to a main scan is too low, or the threshold THguide for guidance is too high. In order to prevent a delay in a main scan, it is important to avoid such a situation. For this reason, a method of setting the threshold THmain for a shift to a main scan and the threshold THguide for guidance is devised.

The main scan is continued until a finishing condition is satisfied, e.g., a planned continuation time has elapsed, the planned number of rotations is attained, and the contrast medium density (CT average) has decreased to a predetermined value or data acquisition in a predetermined helical scan range is completed in a helical scan (S14). When such conditions are satisfied, the main scan is finished (S15).

As described above, according to this embodiment, not only the threshold THmain for a main scan but also the threshold THguide for voice guidance are set, and guidance is automatically output at time t1 when the CT average has reached the threshold THguide for guidance. This makes it possible to eliminate a delay from time t2 when the CT average has reached the threshold THmain for a main scan to the start of the main scan. In addition, even if a guidance or waiting time has not elapsed at time t2 when the CT average has reached the threshold THmain for a main scan, the delay time from time t2 to the start of the main scan can always be shortened as compared with the total time of the guidance time and waiting time.

Figure 7:
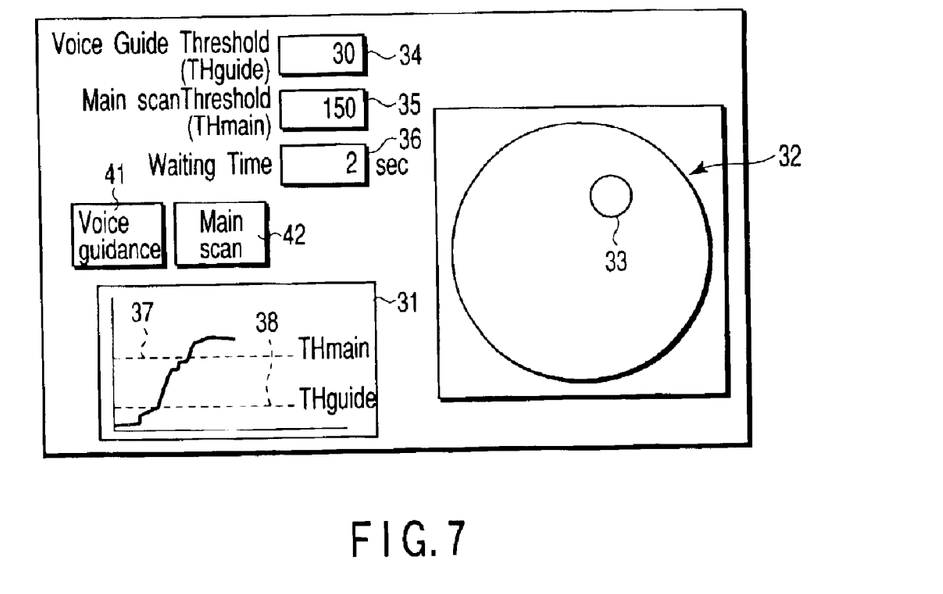
FIG. 7 is a view showing an example of the threshold setting window displayed on an operation window of an operation console or a display unit under the control of a scan controlling unit in FIG. 2.

FIG. 7 shows a setting window for real preparation conditions (the size and position of the region of interest ROI, the two types of thresholds THguide and THmain, and the waiting time WT) to be displayed on the operation screen of the console 26 or the displaying unit 25 under the control of the scan controlling unit 21. For condition setting, a tomographic image 32 obtained in advance is displayed on, for example, the right box on the window, and a time density curve 31 is displayed together on the lower left box on the window. As the time density curve 31, variations in the CT average of the real-time image over time which is obtained by a preparation scan are displayed after the start of the preparation scan. When conditions are to be set, however, a standard time density curve model corresponding to an imaging region is displayed.

The data of this time density curve model is associated with the region and stored in the voice data storing unit 27. A mark 33 of the region of interest ROI is superimposed on the tomographic image 32. The operator can move the mark to a desired position on the image by using a pointing device and set a desired size.

In addition, boxes for inputting the thresholds THguide and THmain and the waiting time WT are displayed on the upper left portion on the setting window. The operator can set the thresholds THguide and THmain and the waiting time by inputting arbitrary numerical values in the respective boxes. The waiting time from the end of guidance is arbitrarily set by an examiner in accordance with the age, physical condition, and the like of the subject. In some case, the waiting time may be set to zero. If the threshold THmain for a main scan is set, the threshold THguide for guidance, e.g., 30% of the threshold THmain, is automatically input as a default value. This allows the operator to manually input the threshold THguide for guidance only when necessary.

Reference lines 37 and 38 on the time density model move up and down in accordance with the thresholds THguide and THmain input in these boxes. The operator can approximate the thresholds THguide and THmain to optimal values while referring to the reference lines and checking the validity of the respective values, the time width between t1 and t2, and the like.

Figure 6:
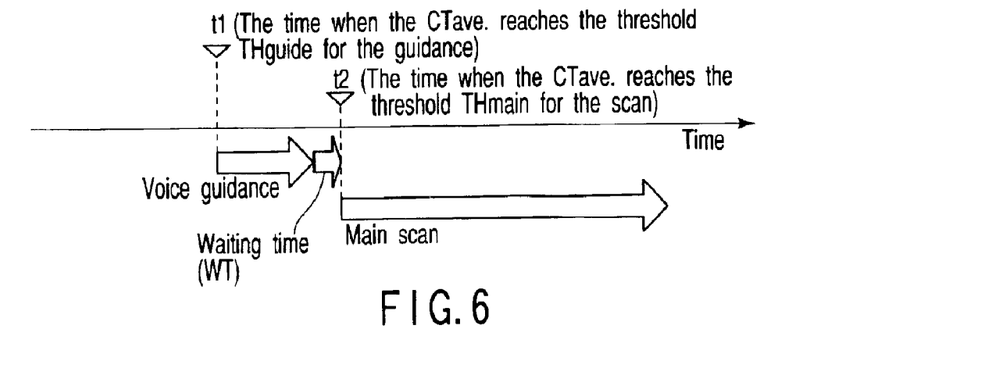
FIG. 6 is a timing chart showing optimized operation from a preparation scan start to a main scan end according to this embodiment.

As shown in FIG. 6, the optimal values of the thresholds THguide and THmain are defined as values that set a state wherein time t2 when the CT average CTave. has reached the threshold THmain for a main scan coincides with the time when the sum of the time required for guidance output and the waiting time has elapsed since time t1 when the CT average CTave. has reached the threshold THguide for guidance. In this state, the constraint time for breath holding by the subject and the like can be minimized. However, the actual time density curve varies among individuals and the curve of the same subject changes depending on uncertainties such as the physical condition. It is therefore impossible in practice to set the thresholds THguide and THmain to optimal values. However, by setting the thresholds THquide and THmain while referring to the time density curve model and automatically inputting the threshold THguide for guidance as a percentage recommended for the threshold THmain for a main scan, the thresholds can be approximated more to optimal values than without these supports.

Figure 8A:
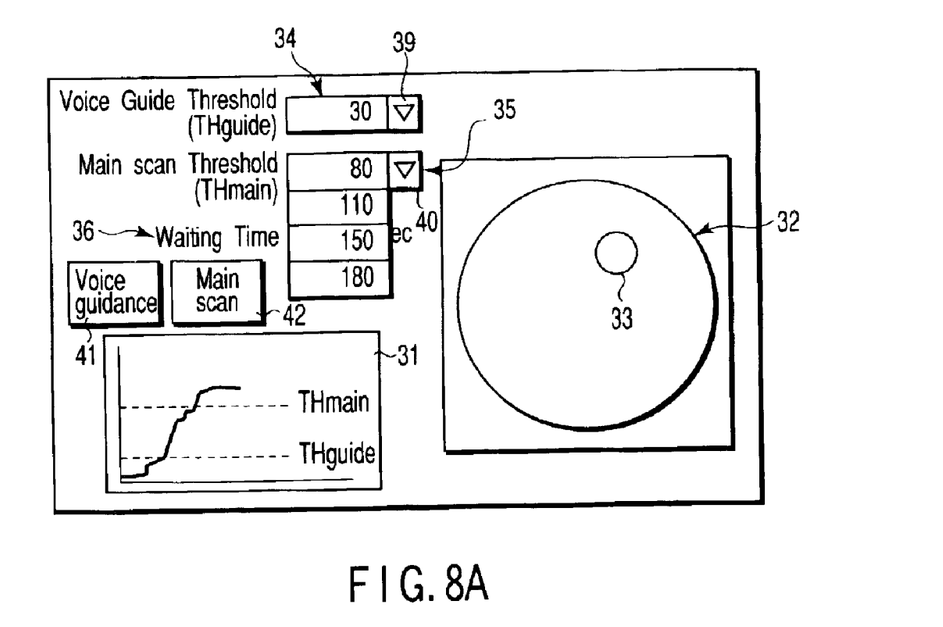
FIGS. 8A and 8B are views showing other examples of the threshold setting window displayed on an operation window of an operation console or a display unit under the control of the scan controlling unit in FIG. 2.
Figure 8B:
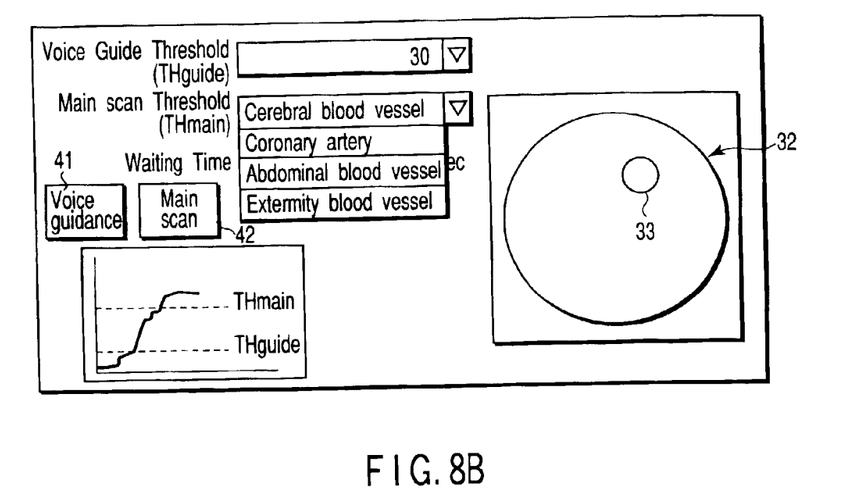

As shown in FIG. 8A, pull-down menus 39 and 40 may be juxtaposed with boxes 34 and 35 for the thresholds THguide and THmain, so that when the pull-down menus are pressed, a plurality of recommended values are displayed in the pull-down menus to allow the examiner to select values from them. As shown in FIG. 8B, a menu of a plurality of regions to be examined may be displayed in place of the recommended values. In this case, the recommenced values of the thresholds THguide and THmain are set for each region to be examined.

Note that the window shown in FIG. 7 is also displayed in the interval between the start of a preparation scan and the end of a main scan. In this interval, a time density curve is generated in accordance with the actual average CTave. calculated in real time and displayed together with the tomographic image 32 reconstructed in real time. This actual time density curve may greatly deviate from the time density curve model used to set the thresholds. In this case, the output timing of voice guidance and the main scan start timing greatly deviate. In order to compensate for such timing deviations, a voice guidance manual button 41 and main scan manual button 42 are prepared. When the operator presses the voice guidance manual button 41, the scan controlling unit 21 cancels the function of automatically outputting voice guidance and forcibly outputs voice guidance. When the operator presses the main scan manual button 42, the scan controlling unit 21 cancels the function of automatically starting a main scan and forcibly starts a main scan. The operator presses the voice guidance manual button 41 as needed while seeing the time density curve displayed in real time. In addition, the operator presses the main scan manual button 42 as needed while seeing the time density curve displayed in real time.

Figure 9:
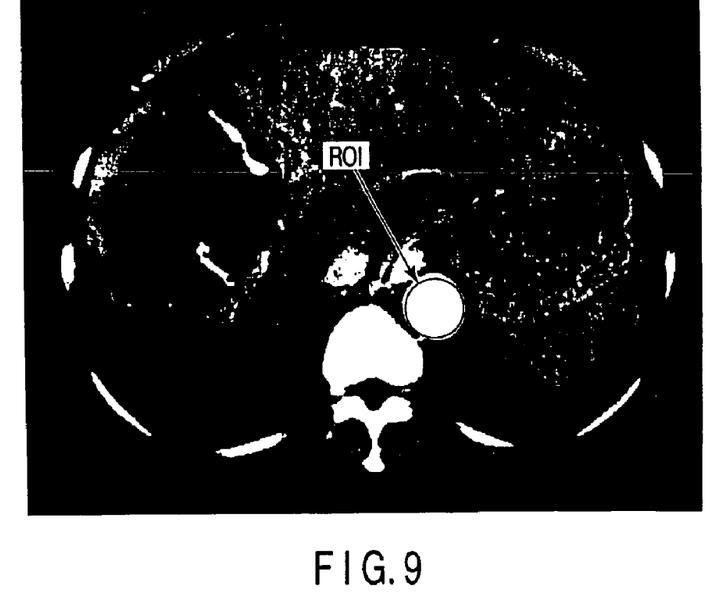
FIG. 9 is a view showing an example of a region of interest ROI set through the operation console in FIG. 2.

In this case, as shown in FIG. 9, the region of interest ROI is set at a proper density monitoring region (descending aorta or the like) located upstream of a slice in a main scan, the average of the CT values of pixels in the region of interest ROI is calculated, and the average is compared with the thresholds THguide and THmain. However, body movement accompanying breath holding may move the region of interest ROI outside the density monitoring region. This is because the region of interest ROI is fixed, but the density monitoring region moves upon breathing. If the region of interest ROI moves outside the density monitoring region, the density monitoring precision decreases. A technique of solving this problem will be described.

Figure 10:
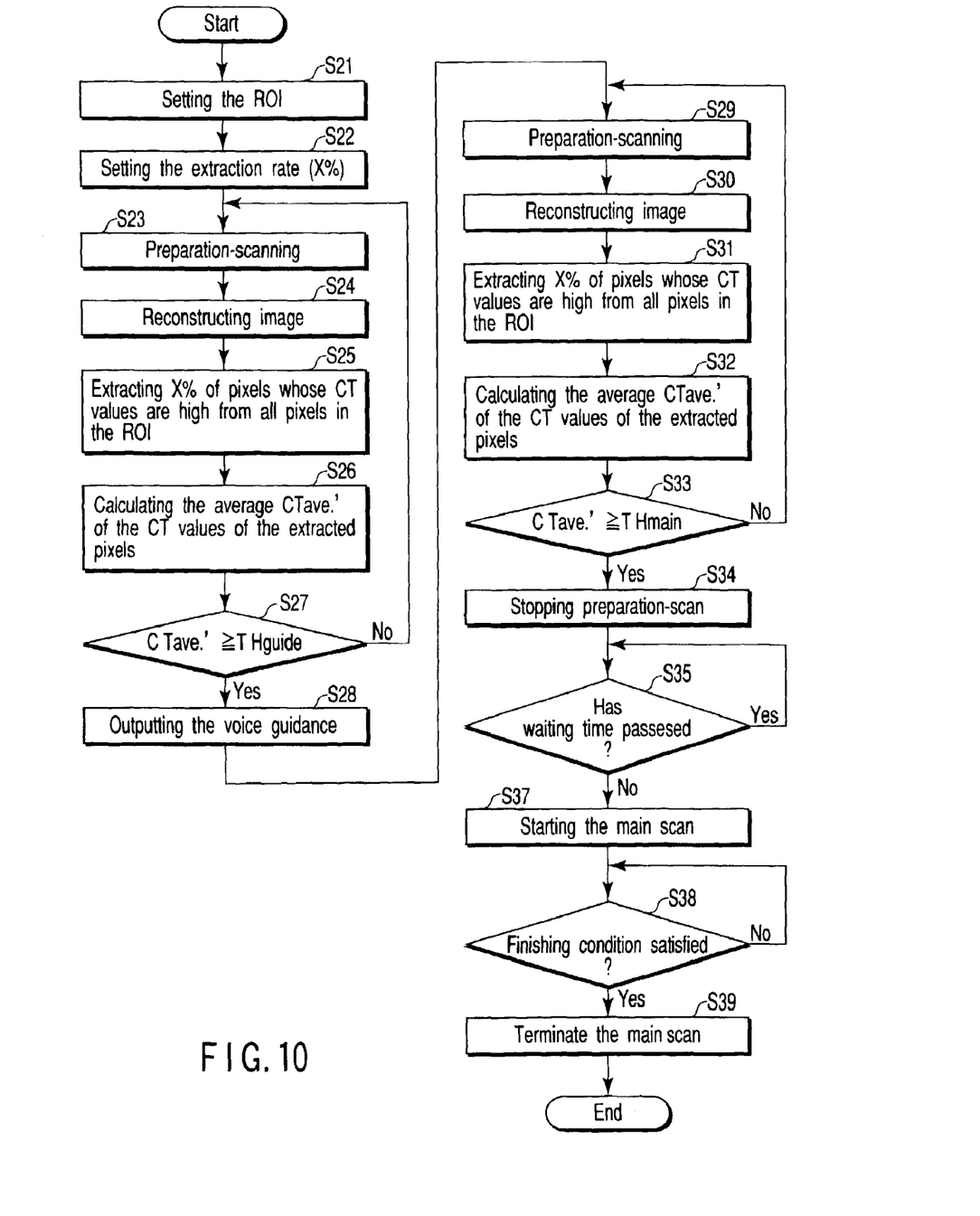
FIG. 10 is a flow chart showing another operation from a preparation scan start to a main scan end according to this embodiment.
Figure 11:
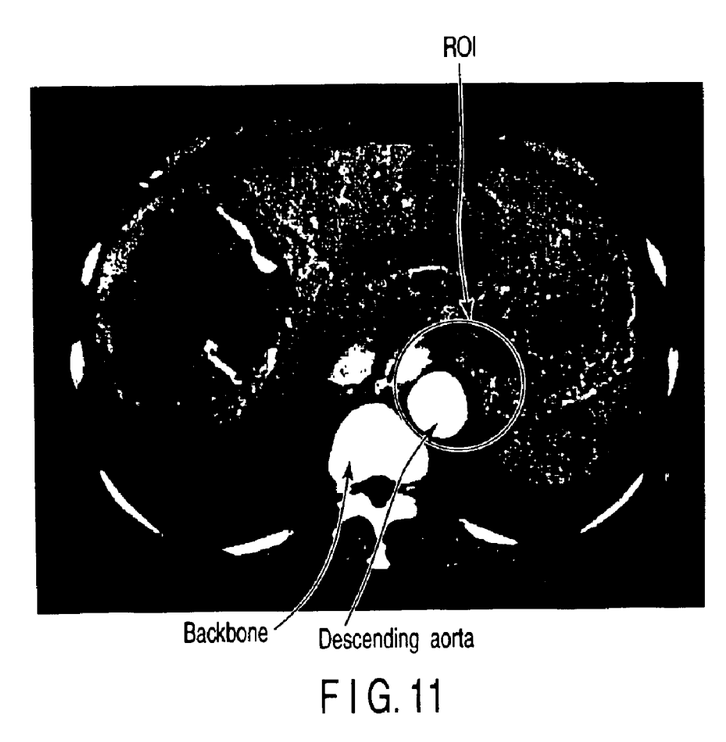
FIG. 11 is a view showing an example of the region of interest ROT set in step S21 in FIG. 10.

FIG. 10 shows an operation procedure for suppressing a deterioration in density monitoring precision due to breathing. First of all, the operator operates the console 26 to set the region of interest ROT on a density monitoring region (e.g., the descending aorta), as shown in FIG. 11 (S21). The region of interest ROI is not limited to a circular shape and can be set in another shape or arbitrary shape. The operator estimates a range in which the density monitoring region moves with breathing, and sets the region of interest ROI to surround the density monitoring region with a large margin so as to include the estimated movement range of the density monitoring region. With this operation, the density monitoring region before the movement is located within the region of interest ROI, and the density monitoring region after the movement is also located within the region of interest ROI. In addition, since the high CT values of the bone decrease the threshold processing precision, the operator should carefully adjust the position, shape, and size of the region of interest ROT, avoiding the bone (backbone or the like) region.

As described above, since the region of interest ROI is set to be larger than the density monitoring region, the region of interest ROT includes a contrast medium flowing into the density monitoring region and the neighboring tissue. For this reason, the average of the CT values of pixels included in the region of interest ROI decreases due to the CT values of the neighboring tissue.

Figure 12:
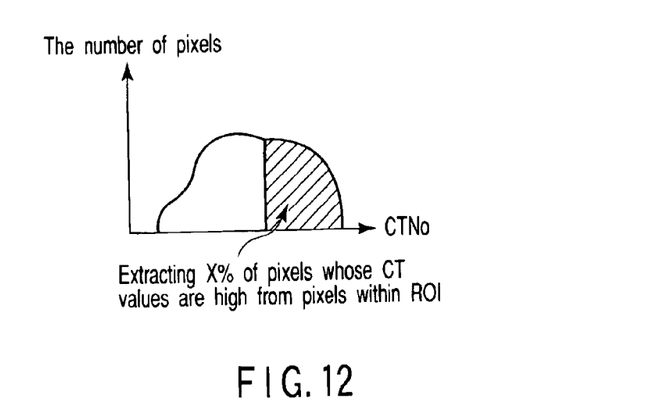
FIG. 12 is a graph for a supplementary explanation of step S25 in FIG. 10.

In order to solve this problem, as shown in FIG. 12, the scan controlling unit 21 has the function of extracting several or several ten % of pixels whose CT values are high from the pixels in the region of interest ROI, and calculating the average of the CT values of the extracted pixels. The above percent is called an extraction rate.

In addition to the region of interest ROI, the corresponding extraction rate is set by the operator through the console 26 (S22). The initial value of the extraction rate is set to 20% that is expected to high in versatility. When the extraction rate is to be changed from the initial value to an arbitrary value, the operator inputs a desired number through the ten keys of the console 26. The scan controlling unit 21 provides pull-down menu at the extraction rate input portion. Various numbers are arranged side by side in the pull-down menu. The operator inputs a desired number from the pull-down menu by operating a pointing device mounted on the console 26.

When the above preparation is complete, a contrast medium is injected into the subject. Thereafter, a real preparation scan is performed under the control of the scan controlling unit 21 (S23), and tomographic image data is reconstructed by the image reconstructing unit 24 (S24).

The scan controlling unit 21 extracts X % of pixels whose CT values are high, which is set as the extraction rate, from the pixels in the relatively large region of interest ROT set in advance (S25). An average CTave.' of the CT values of the extracted pixels is calculated (S26).

The CT average CTave.' is compared with the threshold THguide (S27). If the CT average CTave.' has not reached the threshold THguide, the processing in steps S23 to S27 is repeated. When the CT average CTave.' reaches the threshold THguide, voice guidance concerning breath holding and suppression of body movement is automatically output from the speaker 19 (S28).

Subsequently, a series of operations, e.g., a preparation scan (S29), image reconstruction (S30), extraction of X % of pixels whose CT values are high from pixels in the region of interest ROT (S31), calculation of the average CTave.' of the extracted CT values (S32), and comparison between the threshold THmain and the CT average CTave.' (S33), is repeated until the CT average CTave.' reaches or exceeds the threshold THmain. At this time, a preparation scan is stopped (S34), and the flow waits for the elapse of the waiting time WT as needed (S35, S36). A main scan is then started (S37). The main scan is continued until a finishing condition is satisfied, e.g., a planned continuation time has elapsed, the planned number of rotations is attained, and the contrast medium density (CT average) has decreased to a predetermined value or data acquisition in a predetermined helical scan range is completed in a helical scan (S38). When the condition is satisfied, the main scan is terminated (S39).

In this manner, the region of interest ROI is set to be larger than the density monitoring region, X % pixels whose CT values are high are extracted from pixels in the region of interest ROI, the average of the CT values of the extracted pixels is calculated, and threshold processing is executed with this average, thereby reducing the deviations of the guidance output timing and main scan start timing accompanying the shift of the region of interest ROI from the density monitoring region due to breathing.

In this case, as described above, the operator should carefully adjust the position, shape, and size of the region of interest ROI, avoiding the bone (backbone or the like) region. However, the amplitude of breathing varies in magnitude among individuals, and hence the bone region may enter the region of interest ROI. In this case, since the bone has a high CT value, the guidance output timing and main scan start timing arrive earlier than the planned timings.

Figure 13:
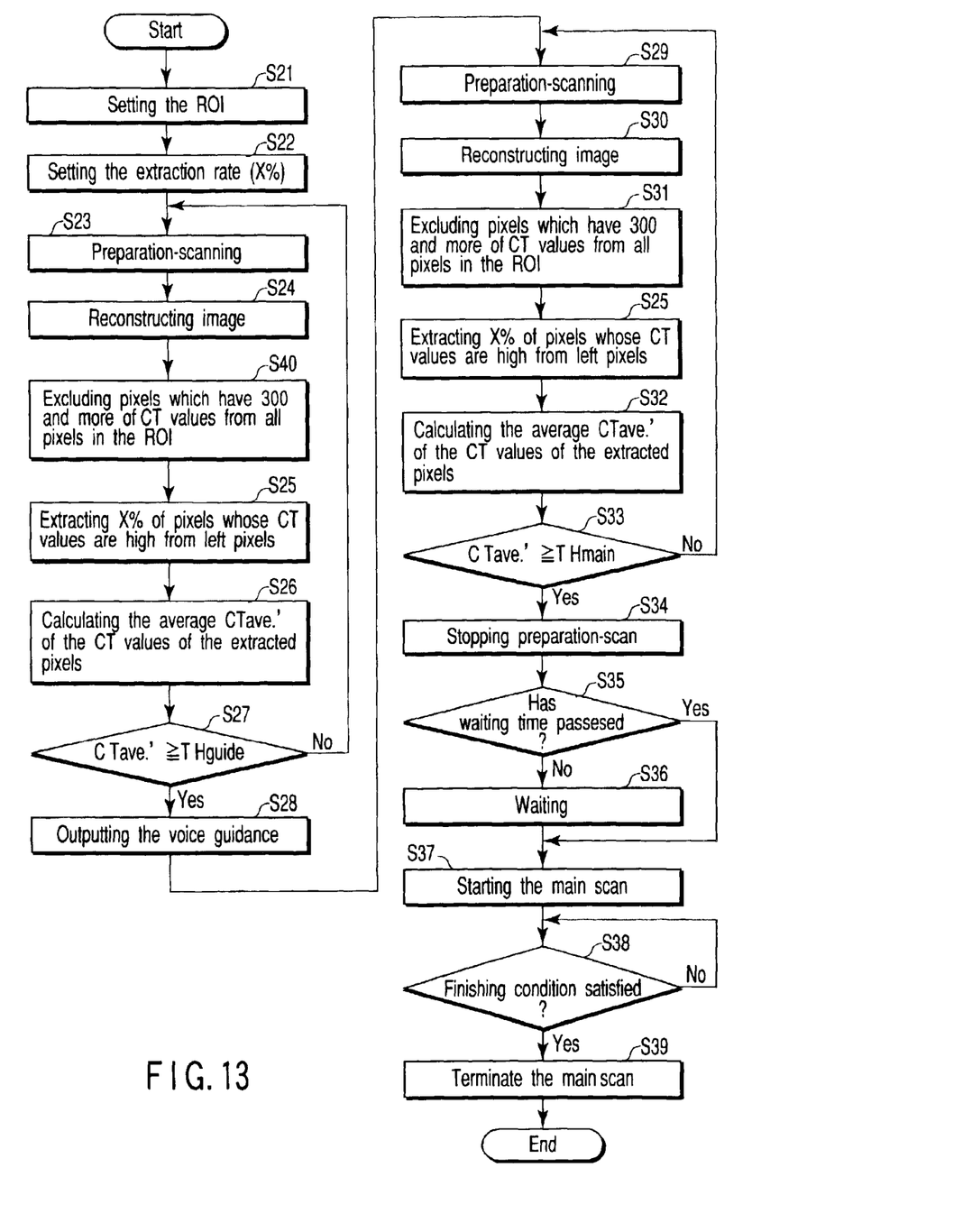
FIG. 13 is a flow chart showing still another operation from a preparation scan start to a main scan end according to this embodiment.

In order to avoid this situation, as shown in FIG. 13, the scan controlling unit 21 removes pixels having CT values higher than a predetermined value from the pixels in the region of interest ROI before the pixel extraction processing in steps S25 and S31 (S40, S41). In general, the CT values of the bone are distributed in the range of 250 to 1,000. The above predetermined value is set to a CT value slightly higher than the lowest CT value (250) of the bone, e.g., 300. By setting the predetermined value to be slightly higher than the lowest CT value (250) of the bone, a slight margin can be provided for a case wherein the CT values of a contrast medium are removed together with the CT values of the bone.

In step S25, pixels having CT values equal to or higher than 300 are removed from the pixels in the region of interest ROI, and the average of the remaining pixels having CT values less than 300 is calculated.

In step S22 in FIG. 10, when the region of interest ROI is set in a complicated shape, the extraction rate may greatly deviate from an optimal value. If the extraction rate is too high, the guidance output timing and the main scan start timing may arrive earlier than the planned timings, and vice versa.

Figure 14:
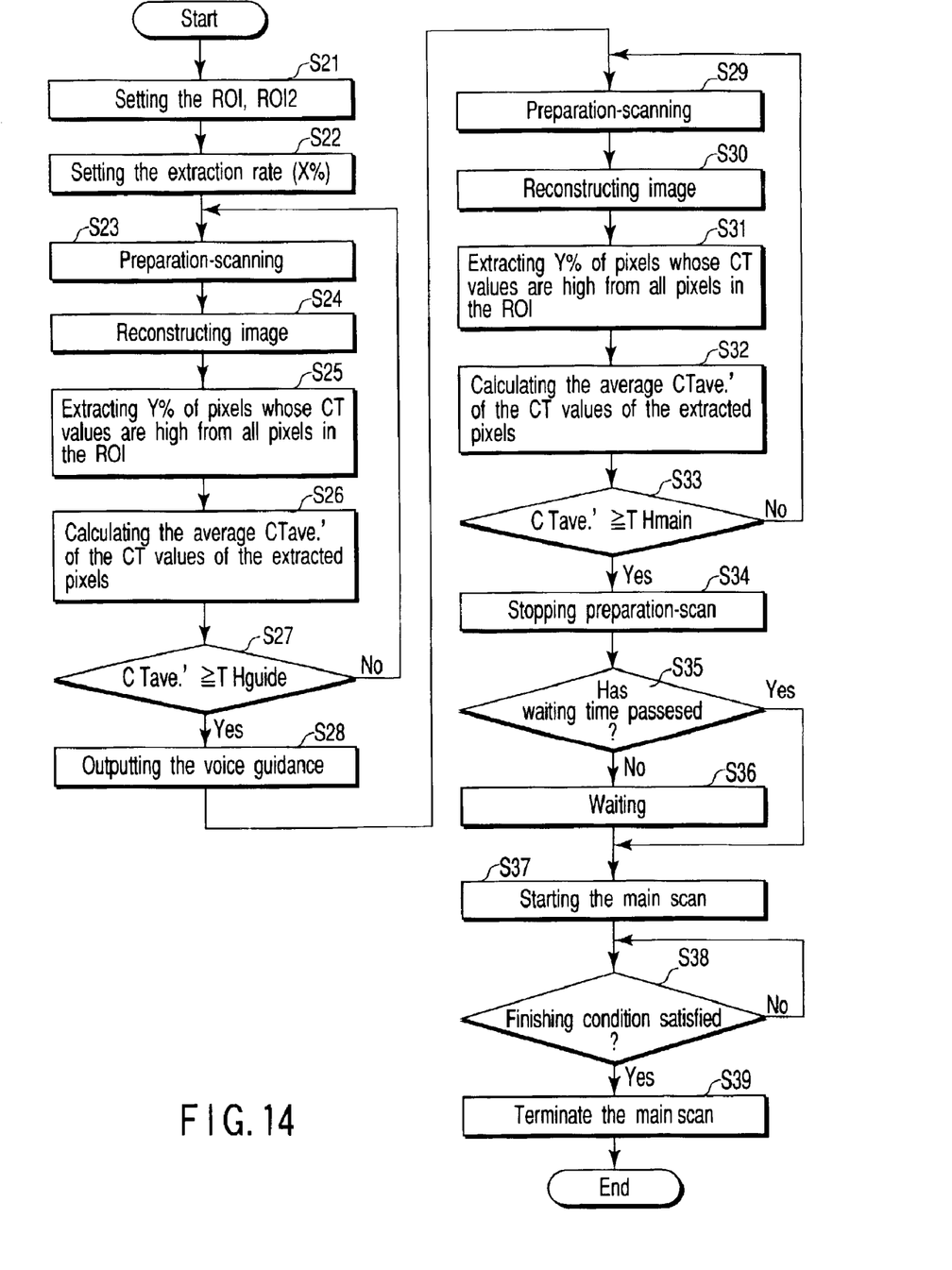
FIG. 14 is a flow chart showing still another operation from a preparation scan start to a main scan end according to this embodiment.
Figure 15:
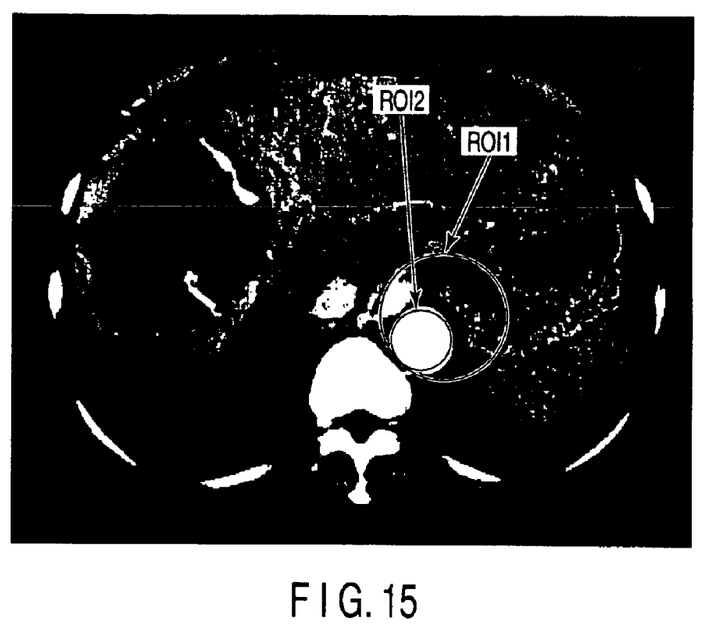
FIG. 15 a view for a supplementary explanation of step S42 in FIG. 14.

In order to reduce this possibility, as shown in FIGS. 14 and 15, two types of regions of interest ROI1 and ROI2 may be set (S42), and the area ratio (ROI2/ROI1) of the two regions, which is calculated by the scan controlling unit 21 (S43), may be set as an extraction rate. In practice, the area ratio may be calculated as the ratio between the numbers of pixels.

The region of interest ROI1 is set to a relatively large size so that the region surrounds a density monitoring region with a large margin, whereas the region of interest ROI2 is set to a relatively small size almost equal to the density monitoring region. The scan controlling unit 21 calculate the area of the region of interest ROI1. For example, the area is represented by the number of pixels. The scan controlling unit 21 also calculates the area of the region of interest ROI2. The scan controlling unit 21 calculates the ratio of the area of the region of interest ROI2 to the area of the region of interest ROI1. If, for example, the area of the region of interest ROI1 is 40 mm$^2$ and the area of the region of interest ROI2 is 10 mm$^2$, the extraction rate is set to 10/40, i.e., 25%.

By setting the extraction rate in this manner, the deviations of the guidance output timing and main scan start timing due to an extraction rate error can be reduced.

Figure 16:
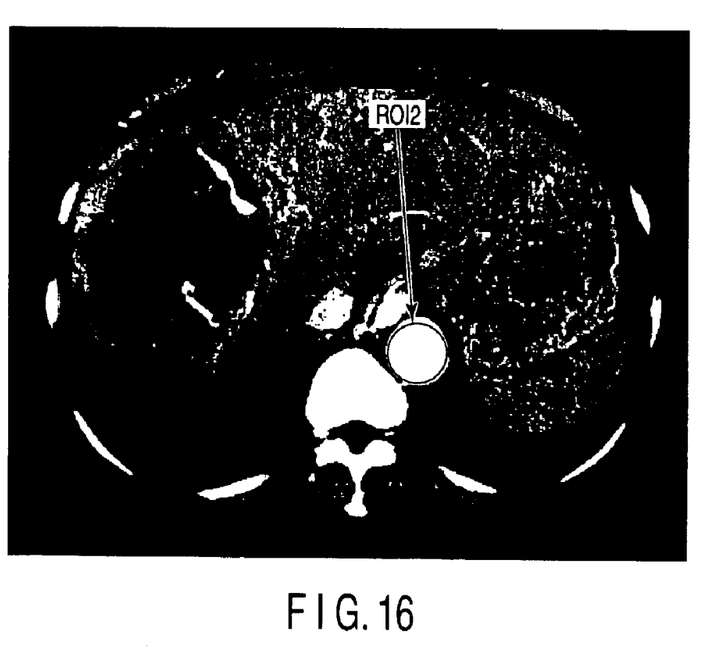
FIG. 16 is a view showing another method of setting the region of interest ROI according to this embodiment.

As shown in FIG. 16, the operator may manually set only the relatively small region of interest ROI2 almost equal to the density monitoring region. In this case, the scan controlling unit 21 automatically sets the region of interest ROI1 having a relatively large size so that the region surrounds the density monitoring region with a large margin on the basis of the manually set region of interest ROI2. For example, the region of interest ROI1 is set by enlarging the region of interest ROI2 radially from the center of gravity of the region of interest ROI2.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus which monitors a density of a contrast medium injected into a subject to be examined with a CT value or a value derived therefrom by repeated preparation scans so as to adjust a main scan start timing that differs in scan condition from the preparation scans, comprising:

a guidance output unit configured to output guidance to the subject; and a control unit configured to compare a CT value of each tomographic image obtained by the preparation scans or a value derived therefrom with a first threshold, supply guidance data to the guidance output unit or control the guidance output unit to output the guidance to the subject when the CT value or the value derived therefrom has reached the first threshold, compare the CT value of each tomographic image obtained by the preparation scans or the value derived therefrom with a second threshold different from the first threshold, and start executing the main scan or preparing the execution of the main scan when the CT value or the value derived therefrom has reached the second threshold.

2. An apparatus according to claim 1, wherein the second threshold is higher than the first threshold.

3. An apparatus according to claim 1, wherein the guidance output unit outputs the guidance by voice and/or picture.

4. An apparatus according to claim 1, wherein the control unit stops the preparation scan and starts executing the main scans or a preparation for the execution when the CT value or the value derived therefrom reaches the second threshold.

5. An apparatus according to claim 1, further comprising an operation unit by which an operator sets at least one of the first and second thresholds.

6. An apparatus according to claim 5, wherein the first threshold is set by the control unit on the basis of the second threshold set through the operation unit.

7. An apparatus according to claim 5, wherein the control unit displays a plurality of recommended values or a plurality of candidate values associated with at least one of the first and second thresholds on an operation window of the operation unit.

8. An apparatus according to claim 5, wherein the control unit displays an operation button corresponding to an instruction to output the guidance to the subject on an operation window of the operation unit, and when the operation button is clicked, the control unit supplies guidance data to the guidance output unit or controls the guidance output unit to output the guidance to the subject even if the CT value or the value derived therefrom has not reached the first threshold.

9. An apparatus according to claim 5, wherein the control unit displays an operation button corresponding to an instruction to execute the main scan or start a preparation for the execution on the operation window of the operation unit, and when the operation button is clicked, the operation unit starts executing the main scan or preparing for the execution even if the CT value or the value derived therefrom has not reached the second threshold.

10. An apparatus according to claim 1, wherein the control unit calculates an average of CT values of pixels in a region of interest from each of tomographic images obtained by the preparation scans.

11. An X-ray computed tomography apparatus comprising:

a scan unit configured to scan a subject to be examined with X-rays to acquire projection data about the subject;

a reconstructing unit configured to reconstruct a tomographic image on the basis of the projection data;

a guidance output unit which outputs guidance to the subject, and a control unit configured to compare a CT value of each tomographic image obtained by preparation scans or a value derived therefrom with a first threshold, supply guidance data to the guidance output unit or control the guidance output unit to output the guidance to the subject when the CT value or the value derived therefrom has reached the first threshold, compare the CT value of tomographic image obtained by the preparation scans or the value derived therefrom with a second threshold different from the first threshold, and start executing the main scan or preparing the execution of the main scan when the CT value or the value derived therefrom has reached the second threshold.

12. An X-ray computed tomography apparatus, which monitors a density of a contrast medium injected into a subject to be examined with a CT value or a value derived therefrom by a preparation scans so as to adjust a main scan start timing that differs in scan condition from the preparation scan, comprising:

an X-ray tube;

an X-ray detector;

a high voltage generating unit configured to apply a high voltage to the X-ray tube;

a reconstructing unit configured to reconstruct tomographic image data on the basis of an output from the X-ray detector;

an operation unit configured to set a region of interest with respect to the tomographic image;

a control unit configured to compare a CT value of some pixels in the region of interest or a value derived therefrom with a threshold, and stop the preparation scans and starts executing the main scan or preparing for the execution when the CT value or a value derived therefrom reaches the threshold; and wherein the control unit removes pixels having CT values equal to or higher than a predetermined value from the pixels in the region of interest, and extracts a predetermined percent of pixels whose CT values are high from the remaining pixels.

13. An apparatus according to claim 12, wherein the control unit extracts a predetermined percent of pixels whose CT values are higher than a predetermined value from pixels in the region of interest, and calculates an average of the CT values of the extracted pixels.

14. An apparatus according to claim 13, wherein the control unit sets a ratio of an area of a density monitoring region to an area of the region of interest to the predetermined percent.

15. An apparatus according to claim 14, wherein another region of interest smaller than the region of interest is set to limit the density monitoring region.

16. An apparatus according to claim 14, further comprising an input unit which sets the region of interest and the other region of interest on a tomographic image.

17. An apparatus according to claim 12, wherein the control unit removes pixels having CT values equal to or higher than a predetermined value from the pixels in the region of interest.

* * * * *